US011350848B2

(12) United States Patent
Averina et al.

(10) Patent No.: US 11,350,848 B2
(45) Date of Patent: Jun. 7, 2022

(54) SYSTEM AND METHOD FOR GENERATING A TREND PARAMETER BASED ON RESPIRATION RATE DISTRIBUTION

(71) Applicant: CARDIAC PACEMAKERS, INC., St. Paul, MN (US)

(72) Inventors: Viktoria Averina, Roseville, MN (US); Yi Zhang, Plymouth, MN (US); Yousufali Dalal, Northridge, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 242 days.

(21) Appl. No.: 13/763,941

(22) Filed: Feb. 11, 2013

(65) Prior Publication Data

US 2013/0150745 A1 Jun. 13, 2013
US 2016/0150996 A9 Jun. 2, 2016

Related U.S. Application Data

(63) Continuation of application No. 12/769,020, filed on Apr. 28, 2010, now Pat. No. 8,372,012, which is a
(Continued)

(51) Int. Cl.
*A61B 5/08* (2006.01)
*A61B 5/0205* (2006.01)
*C07C 17/361* (2006.01)

(52) U.S. Cl.
CPC .......... *A61B 5/0803* (2013.01); *A61B 5/0205* (2013.01); *A61B 5/0816* (2013.01); *A61B 5/08* (2013.01); *C07C 17/361* (2013.01)

(58) Field of Classification Search
CPC ....... A61B 5/0816; A61B 5/4818; A61B 5/08; A61B 5/0205; A61B 5/0803
(Continued)

(56) References Cited

U.S. PATENT DOCUMENTS 4,562,841 A 1/1986 Brockway et al.
4,928,688 A 5/1990 Mower
(Continued)

OTHER PUBLICATIONS

Ekman et al., "Symptoms in Patients with Heart Failure are Prognostic Predictors: Insights from COMET," Journal of Cardiac Failure, 2005, p. 288-292, vol. 11, No. 4.
(Continued)

*Primary Examiner* — Christian Jang
*Assistant Examiner* — Karen E Toth
(74) *Attorney, Agent, or Firm* — Schwegman Lundberg & Woessner, P.A.

(57) ABSTRACT

Systems and methods provide for assessing the heart failure status of a patient and, more particularly, to generating a trend parameter based on a distribution of the patient's respiration rate. Systems and methods provide for detecting, using an implantable device or a patient-external device, patient respiration and computing a respiration rate based on the detected patient respiration. A distribution of the respiration rate is calculated, and a trend parameter based on the respiration rate distribution is generated. The trend parameter is indicative of a patient's heart failure status. An output signal indicative of the patient's heart failure status may be generated based on the trend parameter.

17 Claims, 12 Drawing Sheets

Related U.S. Application Data continuation of application No. 11/438,977, filed on May 23, 2006, now Pat. No. 7,731,663.

(60) Provisional application No. 60/717,983, filed on Sep. 16, 2005.

(58) Field of Classification Search
USPC .................................. 600/484, 538, 529
See application file for complete search history.

(56) References Cited

U.S. PATENT DOCUMENTS

| | | | |
|---|---|---|---|
| 5,036,849 A | 8/1991 | Hauck et al. | |
| 5,133,353 A | 7/1992 | Hauser | |
| 5,179,945 A | 1/1993 | Van Hofwegen et al. | |
| 5,203,348 A | 4/1993 | Dahl et al. | |
| 5,230,337 A | 7/1993 | Dahl et al. | |
| 5,284,136 A | 2/1994 | Hauck et al. | |
| 5,313,953 A | 5/1994 | Yomtov et al. | |
| 5,314,459 A | 5/1994 | Swanson et al. | |
| 5,318,597 A | 6/1994 | Hauck | |
| 5,334,222 A | 8/1994 | Salo et al. | |
| 5,360,442 A | 11/1994 | Dahl et al. | |
| 5,366,496 A | 11/1994 | Dahl et al. | |
| 5,376,106 A | 12/1994 | Stahmann | |
| 5,388,578 A | 2/1995 | Yomtov et al. | |
| 5,391,200 A | 2/1995 | KenKnight | |
| 5,397,342 A | 3/1995 | Heil et al. | |
| 5,411,031 A | 5/1995 | Yomtov et al. | |
| 5,540,727 A | 7/1996 | Tockman et al. | |
| 5,545,202 A | 8/1996 | Dahl et al. | |
| 5,603,732 A | 2/1997 | Dahl et al. | |
| 5,620,466 A | 4/1997 | Haefner et al. | |
| 5,662,688 A | 9/1997 | Haefner et al. | |
| 5,682,898 A * | 11/1997 | Aung et al. | 600/484 |
| 5,836,987 A | 11/1998 | Baumann et al. | |
| 5,916,243 A | 6/1999 | Kenknight et al. | |
| 6,026,320 A | 2/2000 | Carlson et al. | |
| 6,044,298 A | 3/2000 | Salo et al. | |
| 6,055,454 A | 4/2000 | Heemels | |
| 6,162,183 A * | 12/2000 | Hoover | 600/534 |
| 6,211,011 B1 | 4/2001 | Chen | |
| 6,270,457 B1 | 8/2001 | Bardy | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,358,201 B1 * | 3/2002 | Childre et al. | 600/300 |
| 6,358,203 B2 | 3/2002 | Bardy | |
| 6,360,127 B1 | 3/2002 | Ding et al. | |
| 6,368,284 B1 | 4/2002 | Bardy | |
| 6,371,922 B1 | 4/2002 | Baumann | |
| 6,398,728 B1 | 6/2002 | Bardy | |
| 6,411,848 B2 | 6/2002 | Kramer et al. | |
| 6,424,865 B1 | 7/2002 | Ding | |
| 6,440,066 B1 | 8/2002 | Bardy | |
| 6,454,719 B1 * | 9/2002 | Greenhut | 600/484 |
| 6,459,929 B1 | 10/2002 | Hopper et al. | |
| 6,542,775 B2 | 4/2003 | Ding et al. | |
| 6,597,951 B2 | 7/2003 | Kramer et al. | |
| 6,757,414 B1 * | 6/2004 | Turek et al. | 382/128 |
| 6,810,285 B2 | 10/2004 | Pless et al. | |
| 6,993,389 B2 | 1/2006 | Ding et al. | |
| 7,070,568 B1 * | 7/2006 | Koh | 600/508 |
| 7,094,207 B1 * | 8/2006 | Koh | 600/529 |
| 7,260,432 B2 | 8/2007 | Kramer et al. | |
| 7,499,750 B2 | 3/2009 | Haefner et al. | |
| 7,731,663 B2 | 6/2010 | Averina et al. | |
| 8,372,012 B2 | 2/2013 | Averina et al. | |
| 2002/0099302 A1 * | 7/2002 | Bardy | A61B 5/0002 600/510 |
| 2002/0143264 A1 | 10/2002 | Ding et al. | |
| 2003/0004428 A1 * | 1/2003 | Pless et al. | 600/544 |
| 2003/0055461 A1 * | 3/2003 | Girouard | A61B 5/4842 607/17 |
| 2003/0130702 A1 | 7/2003 | Kramer et al. | |
| 2004/0230230 A1 | 11/2004 | Lindstrom et al. | |
| 2004/0230243 A1 | 11/2004 | Haefner et al. | |
| 2005/0080348 A1 * | 4/2005 | Stahmann et al. | 600/529 |
| 2005/0085734 A1 | 4/2005 | Tehrani | |
| 2006/0041281 A1 * | 2/2006 | Von Arx | A61B 5/0215 607/18 |
| 2006/0058686 A1 * | 3/2006 | Berg | A61B 7/04 600/483 |
| 2006/0064030 A1 * | 3/2006 | Cosentino | G01G 23/3742 600/547 |
| 2006/0183174 A1 * | 8/2006 | Ng | G01N 33/573 435/7.92 |
| 2006/0253159 A1 * | 11/2006 | Siejko | A61N 1/3627 607/17 |
| 2006/0270939 A1 * | 11/2006 | Wariar | A61B 7/00 600/528 |
| 2006/0276849 A1 * | 12/2006 | Carlson | A61N 1/36578 607/23 |
| 2007/0073169 A1 * | 3/2007 | Averina et al. | 600/483 |

OTHER PUBLICATIONS

Lee et al., "Predicting Mortality Among Patients Hospitalized for Heart Failure: Derivation and Validation of a Clinical Model," Journal of the American Medical Association, Nov. 19, 2003, p. 2581-2587, vol. 290, No. 19.

Rame et al., "Outcomes after emergency department discharge with a primary diagnosis of heart failure," American Heart Journal, 2001, p. 714-719, vol. 142, No. 4.

Silva et al., "Persistent Orthopnea and the Prognosis of Patients in the Heart Failure Clinic," Congestive Heart Failure, 2004, p. 177-180, vol. 10, No. 4.

"U.S. Appl. No. 11/438,977, 312 Amendment filed Apr. 28, 2010", 4 pgs.

"U.S. Appl. No. 11/438,977, Examiner Interview Summary dated Apr. 23, 2009", 2 pgs.

"U.S. Appl. No. 11/438,977, Final Office Action dated Oct. 16, 2009", 16 pgs.

"U.S. Appl. No. 11/438,977, Non Final Office Action dated Feb. 4, 2009", 15 pgs.

"U.S. Appl. No. 11/438,977, Notice of Allowance dated Jan. 29, 2010", 6 pgs.

"U.S. Appl. No. 11/438,977, PTO Response to Rule 312 Communication dated May 10, 2010", 2 pgs.

"U.S. Appl. No. 11/438,977, Response filed Jul. 6, 2009 to Non Final Office Action dated Feb. 4, 2009", 9 pgs.

"U.S. Appl. No. 11/438,977, Response filed Dec. 16, 2009 to Final Office Action dated Oct. 16, 2009", 8 pgs.

"U.S. Appl. No. 12/769,020, Non Final Office Action dated Jul. 3, 2012", 10 pgs.

"U.S. Appl. No. 12/769,020, Notice of Allowance dated Oct. 9, 2012", 7 pgs.

"U.S. Appl. No. 12/769,020, Response filed Sep. 20, 2012 to Non Final Office Action dated Jul. 3, 2012", 8 pgs.

* cited by examiner

SYSTEM AND METHOD FOR GENERATING A TREND PARAMETER BASED ON RESPIRATION RATE DISTRIBUTION

RELATED APPLICATIONS

This application is a continuation of U.S. patent application Ser. No. 12/769,020 filed on Apr. 28, 2010, which is a continuation of U.S. patent application Ser. No. 11/438,977 filed on May 23, 2006, now U.S. Pat. No. 7,731,663, which claims the benefit of Provisional Patent Application Ser. No. 60/717,983, filed on Sep. 16, 2005, which are hereby incorporated herein by reference.

FIELD OF THE INVENTION

The present invention relates generally to respiration detection and monitoring and, more particularly, to generating a trend parameter based on a distribution of the patient's respiration rate.

BACKGROUND OF THE INVENTION

Rapid shallow breathing (RSB) is a disorder associated with shortness of breath or difficult breathing (the subjective feeling of being out of breath) caused by heart or lung disorders, strenuous activity, high anxiety or stress. One form of RSB, termed dyspnea, derives from interactions among multiple physiological, psychological, social, and environmental factors, and may induce secondary physiological and behavioral responses. Dyspnea is different from tachypnea (rapid breathing) and hyperpnea (deep breathing). Tachypnea and hyperpnea can occur with hyperventilation, or over breathing beyond what is required to maintain arterial blood gases within normal limits. Fear or anxiety may create even more distress in dyspnic patients.

Dyspnea may be classified as chronic, acute, or terminal. Chronic dyspnea has a variable intensity and is associated with persistent shortness of breath. This is most often seen in patients with chronic obstructive pulmonary disease (COPD). Acute dyspnea causes episodes of shortness of breath with high intensity. It may be seen in patients who have suffered a myocardial infarction or pulmonary embolism. Terminal dyspnea occurs in patients with end-stage diseases, and these patients may be in a hospital, at home, or in a hospice. This type of dyspnea is a common complaint in patients with cancer. Dyspnea can be caused by a variety of conditions, including metabolic, allergic, psychiatric, and neuromuscular disorders, and by pain. However, cardiac and pulmonary disorders are the most common causes.

It is estimated that nearly one million hospital admissions for acute decompensated heart failure (HF) occur in the United States each year, which is almost double the number admitted 15 years ago. The re-hospitalization rates during the 6 months following discharge are as much at 50%. Nearly 2% of all hospital admissions in the United States are for decompensated HF patients, and heart failure is the most frequent cause of hospitalization in patients older than 65 years. The average duration of hospitalization is about 6 days. Despite aggressive therapies, hospital admissions for HF continue to increase, reflecting the prevalence of this malady.

SUMMARY OF THE INVENTION

The present invention is directed to systems and methods for assessing heart failure status of a patient and, more particularly, to generating a trend parameter based on a distribution of the patient's respiration rate. The trend parameter may be used to monitor a patient's heart failure status. The trend parameter may also be used to monitor a patient's respiratory disease or disorder.

According to embodiments of the present invention, methods involve detecting patient respiration and computing a respiration rate based on the detected patient respiration. A distribution of the respiration rate is calculated, and a trend parameter based on the respiration rate distribution is generated. An output signal indicative of the patient's heart failure status may be generated based on the trend parameter.

The trend parameter may be used for a variety of purposes, including monitoring the patient's heart failure status, predicting patient decompensation episodes, titrating a patient therapy such as a drug therapy, and initiating triage to the patient or discharging the patient from the hospital based on the trend parameter. The trend parameter may be developed to characterize a respiration rate and a burden of rapid shallow breathing of the patient. The trend parameter may be used to discriminate between stable heart failure status and decompensated heart failure status of the patient. One or both of data and graphs of one or more of the trend parameter, respiration rate, and respiration rate distribution may be displayed.

Calculating a patient's respiration rate distribution may involve generating a histogram from the respiration rate. According to one approach, the trend parameter may be generated based on areas under a curve of the histogram relative to a respiration rate threshold. For example, a first area under a curve of the histogram that falls below the threshold may be computed. The threshold may be determined algorithmically, or preset or determined by a physician or clinician. Generating the trend parameter may involve calculating a ratio of the first area to a total area under the curve of the histogram.

According to another approach, a measure of characteristic respiration rate, such as the mode, mean, median or other statistical measure of interest, for the histogram may be predefined, selected or determined. A measure of distribution spread, such as the standard deviation, interquartile range, or other statistical measure of interest, of the respiration rate distribution may be calculated. Generating the trend parameter may be based on a relationship between the measure of characteristic respiration rate and the measure of respiration rate distribution spread for the histogram. The relationship may be characterized using a plot of the measure of characteristic respiration rate and the measure of respiration rate distribution spread.

One or more of the processes discussed above and elsewhere herein may be performed in a patient-external device or system. One or more of the processes discussed above and elsewhere herein may be performed in an implantable device or system.

In accordance with another embodiment of the present invention, a system includes a medical device comprising sensing circuitry. Detection circuitry is disposed in the medical device and coupled to the sensing circuitry. The detection circuitry is configured to detect one or more respiratory parameters. A processor is coupled to the detection circuitry. The processor is configured to calculate a distribution of the respiration rate developed from the one or more respiratory parameters, and generate a trend parameter based on the respiration rate distribution.

In various embodiments, the device comprising sensing circuitry and detection circuitry is disposed in an implantable medical device. In other embodiments, the device comprising sensing circuitry and detection circuitry is disposed in a patient-external medical device.

The processor may be disposed in an implantable medical device or in a patient-external system. The patient-external system may comprise a networked patient management system, a programmer, or a portable communicator. In one configuration, the processor computes the respiration rate. In another configuration, the detection circuitry computes the respiration rate. The sensing circuitry may include a minute ventilation sensor, a transthoracic impedance sensor, and/or an accelerometer.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
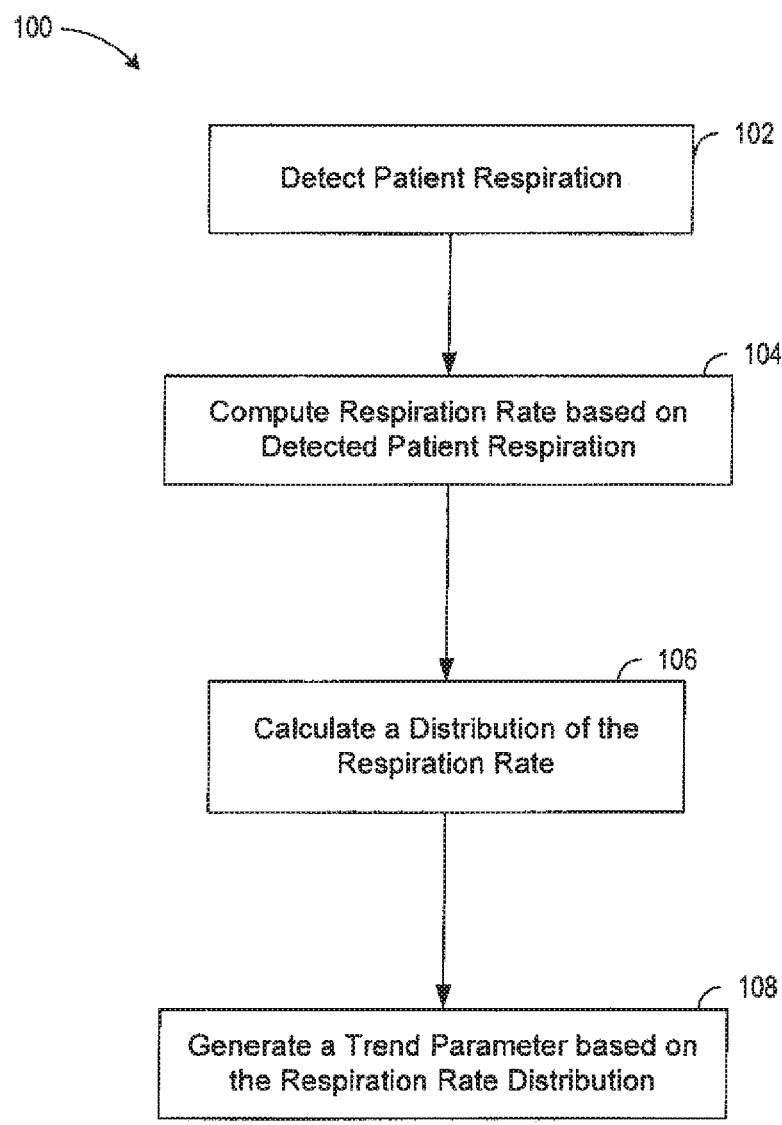
FIG. 1 is a flow diagram of a method for generating a trend parameter based on a distribution of a patient's respiration rate in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A device or system according to the present invention may include one or more of the features, structures, methods, or combinations thereof described hereinbelow. For example, a cardiac monitor, cardiac stimulator, or other type of medical device, including implantable and patient-external devices, may be implemented to include one or more of the advantageous features and/or processes described below. It is intended that such a monitor, stimulator, or other patient-external, implanted or partially implanted device need not include all of the features described herein, but may be implemented to include selected features that provide for useful structures and/or functionality. Such a device may be implemented to provide a variety of therapeutic or diagnostic functions.

A wide variety of medical devices, such as cardiac sensing and/or stimulation devices or other implantable and patient-external medical devices having respiratory sensing capabilities, may be configured to implement a methodology for generating a trend parameter based on a patient's respiration rate distribution in accordance with the present invention. A non-limiting, representative list of such devices includes cardiac monitors, pacemakers, cardiovertors, defibrillators, resynchronizers, and other cardiac sensing and therapy delivery devices.

These devices may be configured with a variety of electrode arrangements, including surface, transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). A variety of devices other than cardiac monitoring/stimulation devices may be implemented to provide for trend parameter generation based on a patient's respiration rate distribution, such as patient-external and implantable drug delivery devices equipped with a respiration sensor arrangement, for example. Such devices are referred to herein generally as a patient-implantable medical device (PIMD) for convenience, it being understood that such a medical device and its functionality may be implemented in a patient-external device or system.

Respiration rate has been shown to be predictive of morality in a HF patient population. Symptoms of dyspnea are among the primary reasons that reduce patients' quality of life and are a primary reason why many HF patients return to the hospital during a HF decompensation episode. When performing long-term trending of HF patients, it is of interest to know how a patient's respiration rate is distributed over a specified time interval. This yields knowledge of how long a patient stays dyspnic so as to relate to the worsening of their I-IF disease state. When the patient spends more time at higher respiration rates, this is indicative of a worsening of their HF status.

Clinical data collected in the ambulatory setting has demonstrated a statistically significant difference between respiration rate distributions from healthy subjects as compared to HF patients. Moreover, there is a statistically significant difference in the pattern for stable HF patients as compared to decompensated HF patients. Information developed from respiration rate data in accordance with the present invention provides for enhanced monitoring and therapy management of HF patients, particularly when the HF status of a patient is in decline.

Methodologies for generating a trend parameter based on a patient's respiration rate distribution in accordance with the present invention advantageously provides physicians with a quantified parameter or index that can be used to monitor a patient's changing HF status and quantitatively evaluate the effectiveness of therapy (e.g., drug or cardiac stimulation therapy) delivered to the patient.

Turning now to FIG. 1, there is illustrated a method 100 for generating a trend parameter based on a patient's respiration rate distribution in accordance with the present invention. According to the method 100, patient respiration is detected 102 using a medical device, such as an implantable or patient-external medical device. Respiration rate is computed 104 based on the detected patient respiration. A distribution of the respiration rate is calculated 106. A trend parameter or index is generated 108 based on the respiration rate distribution.

Figure 2:
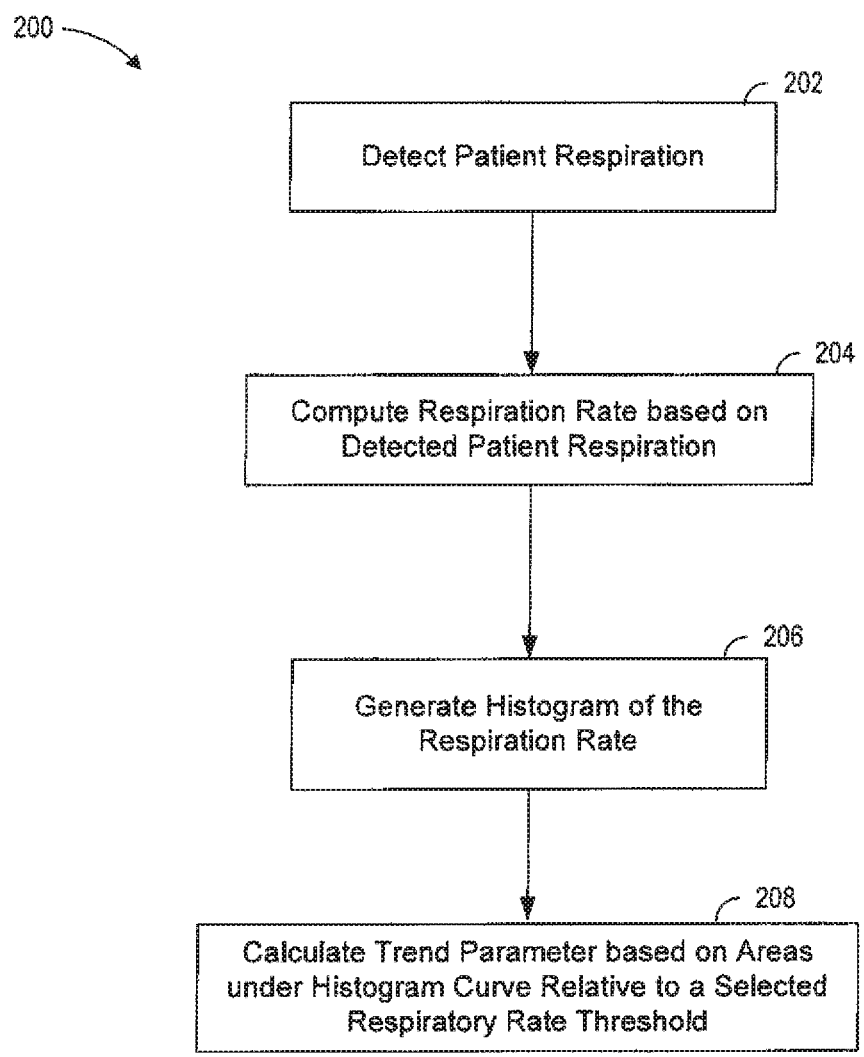
FIG. 2 is a flow diagram of a method for generating a trend parameter based on a distribution of a patient's respiration rate in accordance with other embodiments of the present invention.

By way of example, and in accordance with the method 200 illustrated in FIG. 2, patient respiration is detected 202 using an implantable or patient-external medical device, and respiration rate is computed 204 based on the detected patient respiration. A histogram based on the respiration rate is generated 206. A trend parameter is calculated 208 based on areas under a curve of the histogram relative to a selected, predefined or computed respiration rate threshold.

Figure 3:
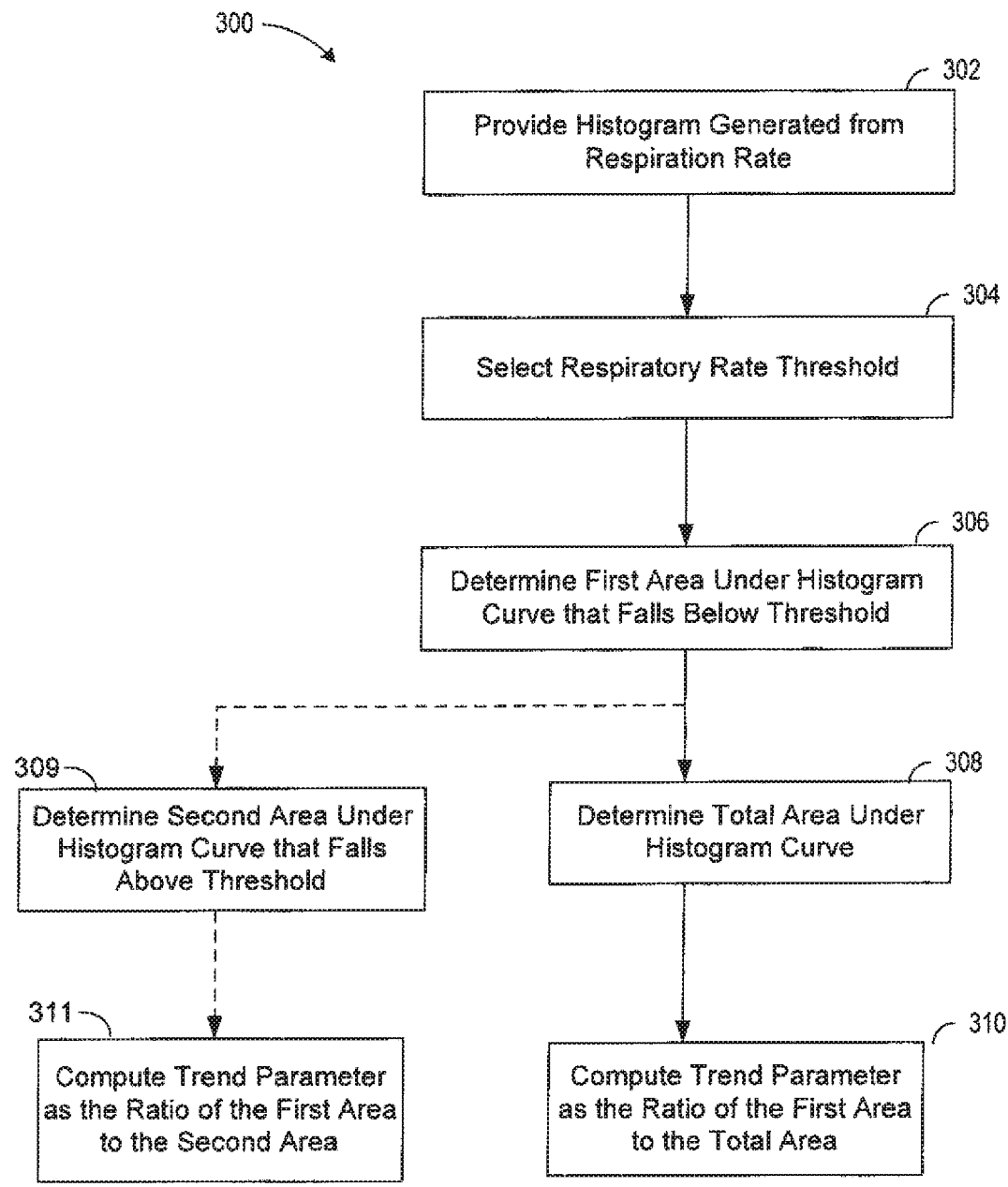
FIG. 3 is a flow diagram of a method for generating a trend parameter based on a distribution of a patient's respiration rate in accordance with further embodiments of the present invention.

In one approach, an example of which is shown in FIG. 3 as method 300, a histogram based on the respiration rate is provided 302. A respiration rate threshold is selected, predefined or computed 304. A first area under a curve of the histogram that falls below the threshold is determined 306. The total area under the histogram curve is computed 308. A trend parameter is computed 310 as the ratio of the first area to the total area under the histogram curve. The respiration rate threshold may be selected or predefined by the physician or clinician, or computed algorithmically, and may represent a single rate or a rate range.

According to a variant of this approach, and as shown in phantom in FIG. 3, a second area under the curve of the histogram that falls above the threshold is determined 309. The trend parameter is computed 311 as the ratio of the first and second areas under the histogram curve.

Figure 5:
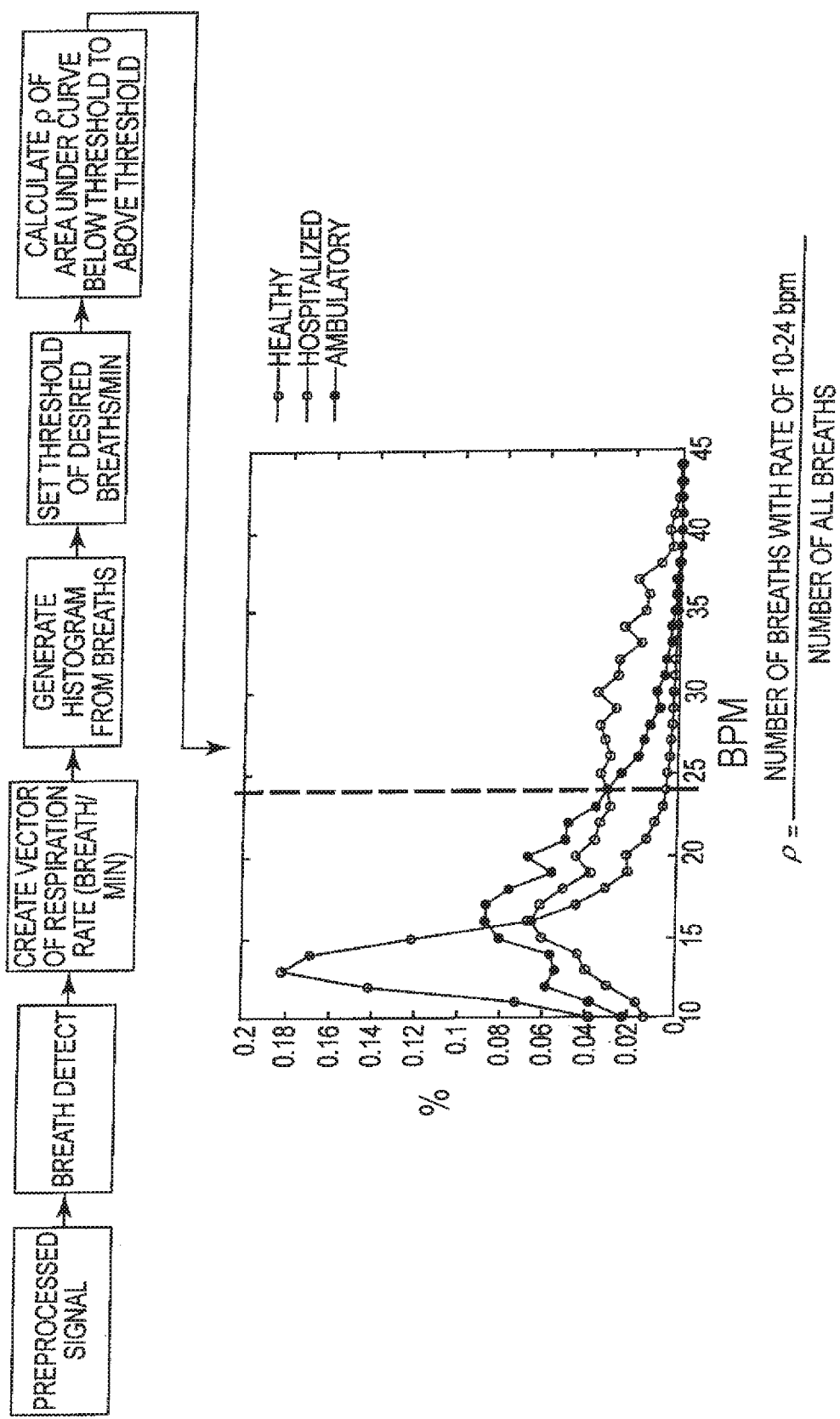
FIG. 5 is an illustration of a process similar to that depicted in FIG. 3 and provides graphical data associated with this approach.

FIG. 5 is an illustration of a process similar to that depicted in FIG. 3 and provides graphical data associated with this approach. The plots of FIG. 5 demonstrate the effectiveness of the trend parameter or index to discern HF status of patients at various HF states. The graphical depiction of the trend parameter in FIG. 5 demonstrates that differences between healthy, hospitalized, and ambulatory HF subjects (and therefore HF status changes in individual subjects) may be reliably determined and monitored.

Figure 4:
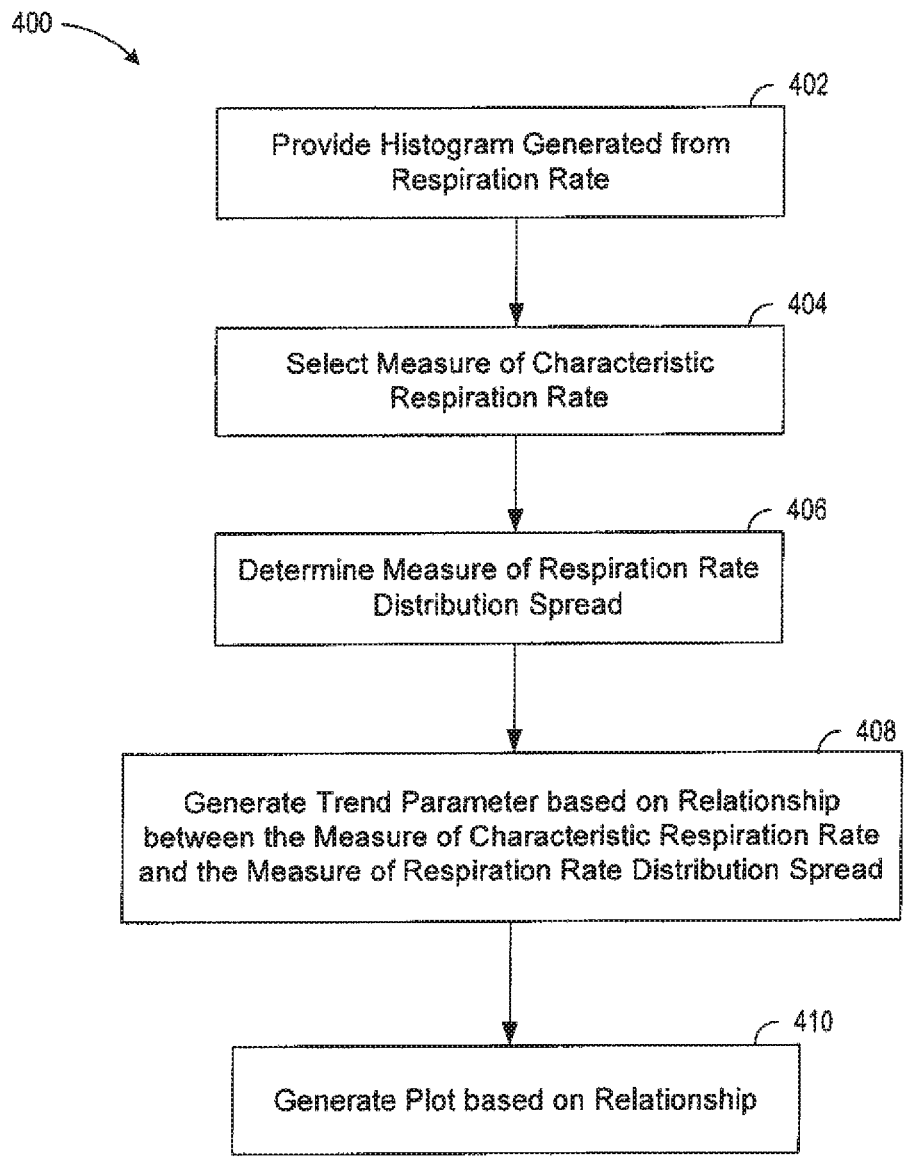
FIG. 4 is a flow diagram of a method for generating a trend parameter based on a distribution of a patient's respiration rate in accordance with other embodiments of the present invention.

FIG. 4 illustrates another approach to generating a trend parameter based on a patient's respiration rate distribution in accordance with the present invention. The method 400 takes into account the characteristic respiration rate (RR) distribution and the spread of the RR distribution to form a more global view of the patient's HF status. The method 400 involves providing 402 a histogram based on the respiration rate. A measure of characteristic respiration rate, such as the mode, mean, median or other statistical measure of interest, for the histogram is predefined, selected or determined 404. A measure of distribution spread, such as the standard deviation, interquartile range, or other statistical measure of interest, of the respiration rate distribution is calculated 406.

Figure 6:
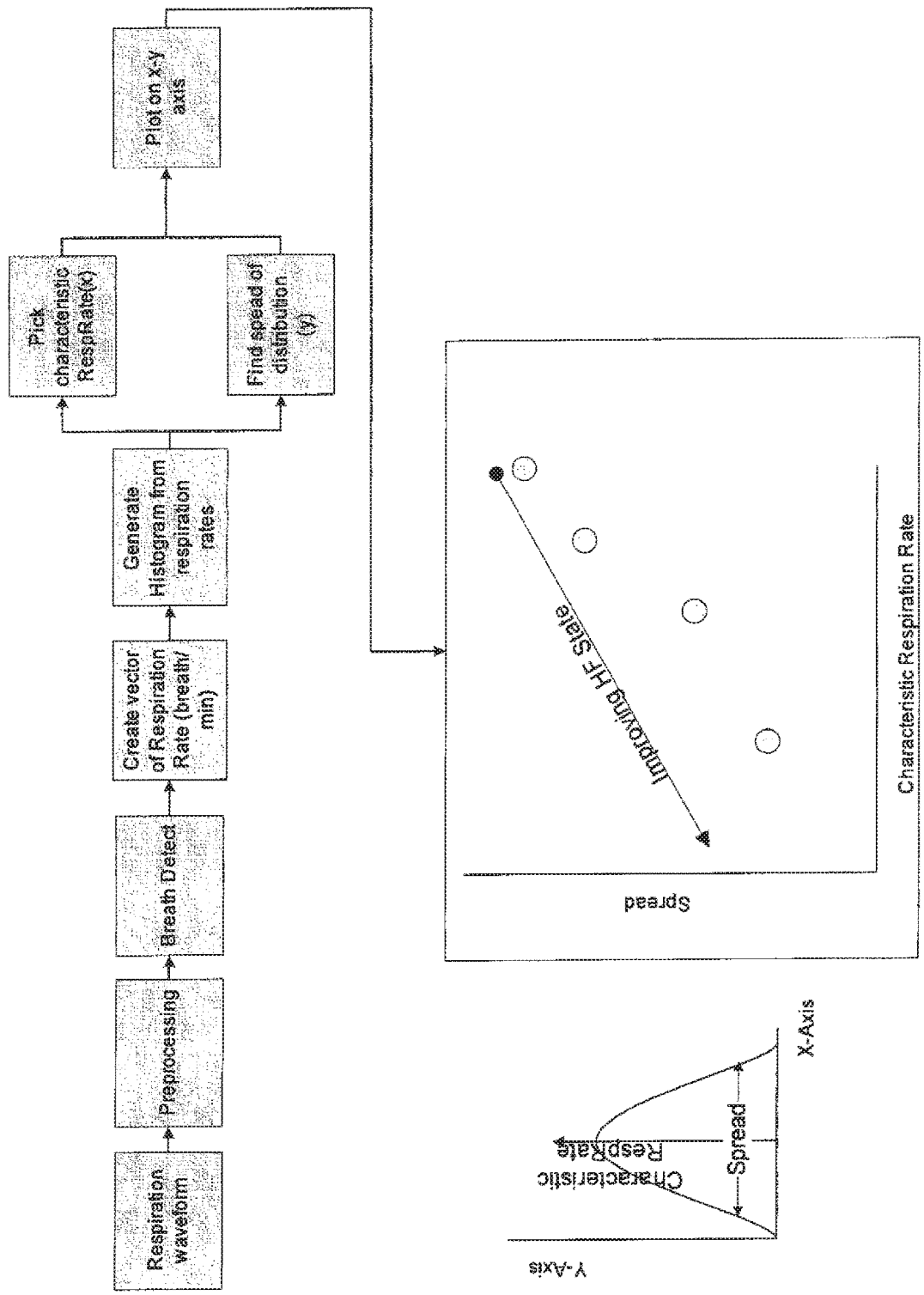
FIG. 6 is an illustration of a process similar to that depicted in FIG. 4 and provides graphical data associated with this approach.

A trend parameter is generated 408 based on a relationship between the measure of characteristic respiration rate and the measure of respiration rate distribution spread for the histogram. A plot or other display of the relationship between the measure of characteristic respiration rate and the measure of respiration rate distribution spread for the histogram may be generated 410. FIG. 6 is an illustration of a process similar to that depicted in FIG. 4 and provides graphical data associated with this approach.

Figure 7:
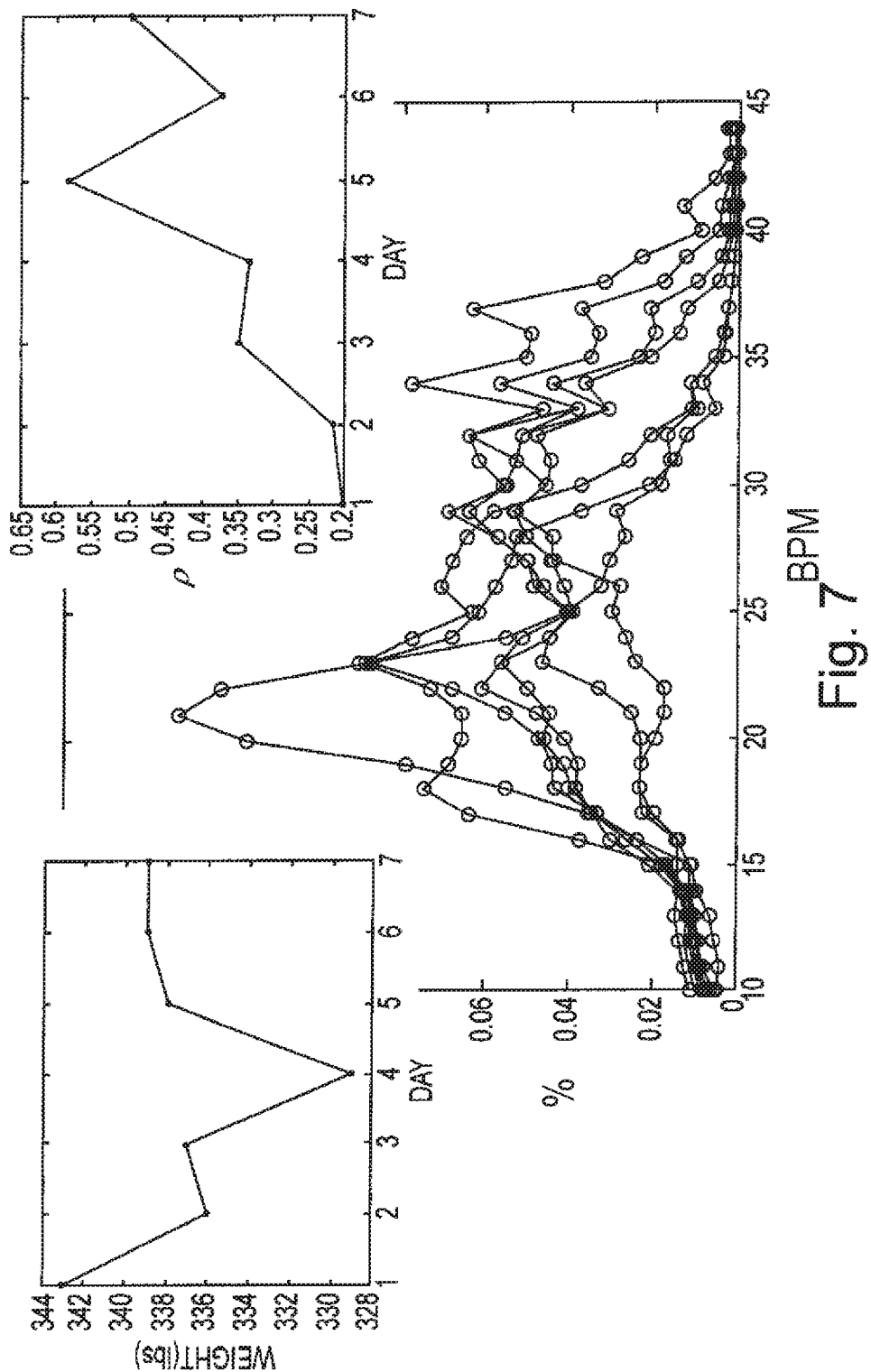
FIG. 7 illustrates patient data showing the performance of monitoring a patient's HF status using a trend parameter generated from a patient's respiration rate distribution in accordance with the present invention.

FIG. 7 illustrates patient data showing the performance of monitoring a patient's HF status using a trend parameter generated from a patient's respiration rate distribution in accordance with the present invention. FIG. 7 further shows a patient's change in weight on a day-to-day basis, and the correlation of trending parameter and patient weight change data as can be seen in the two upper plots of FIG. 7.

Figure 8:
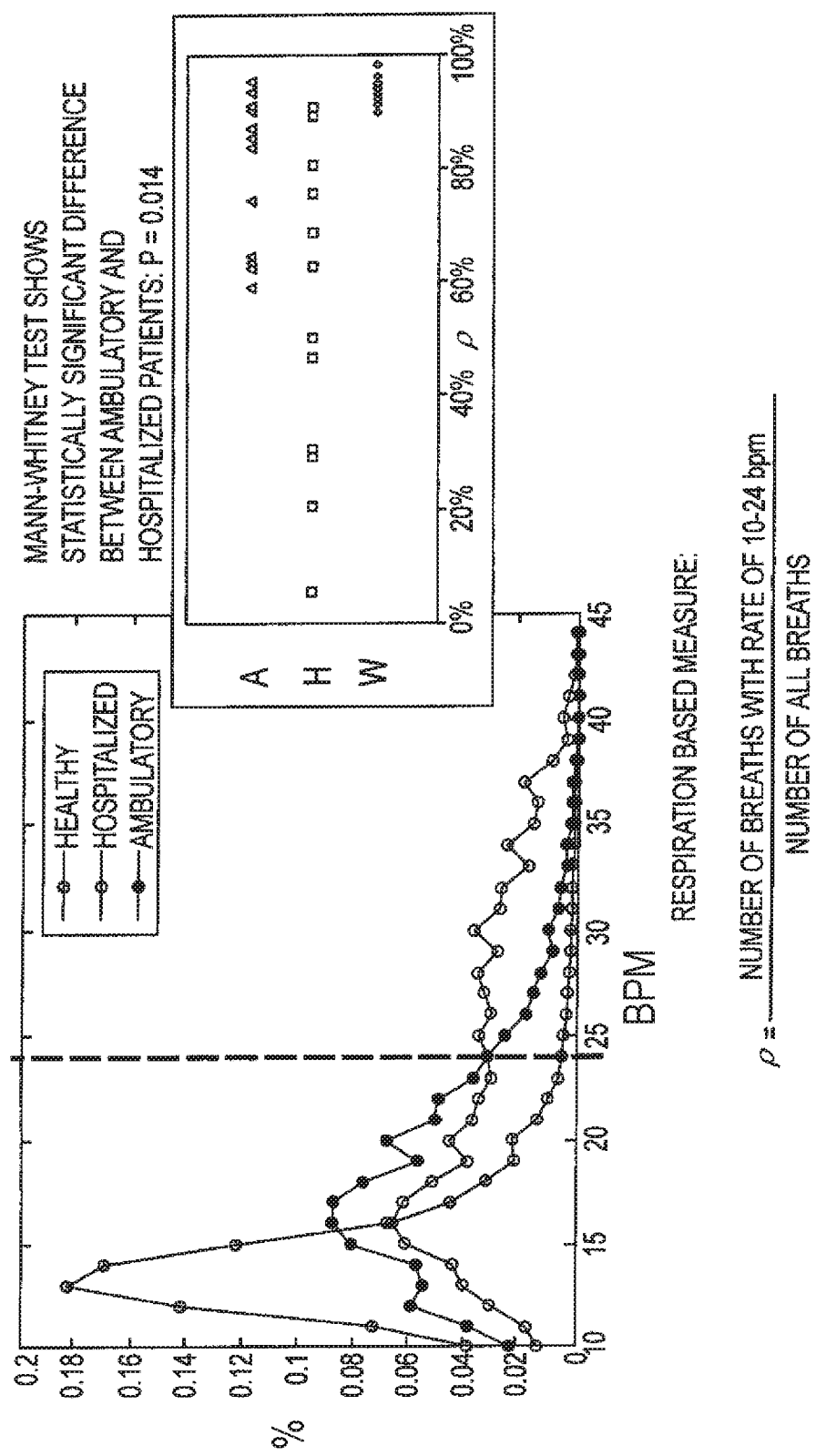
FIG. 8 is a reiteration of the plot shown in FIG. 5, with additional test data superimposed in the figure.

FIG. 8 is a reiteration of the plot shown in FIG. 5, with Mann-Whitney test data superimposed in the figure. The Mann-Whitney test data shows statistically significant differences between ambulatory and hospitalized HF patients, again demonstrating the effectiveness of a trend parameter generated in accordance with the present invention to detect changes in a patient's HF status.

Figure 9:
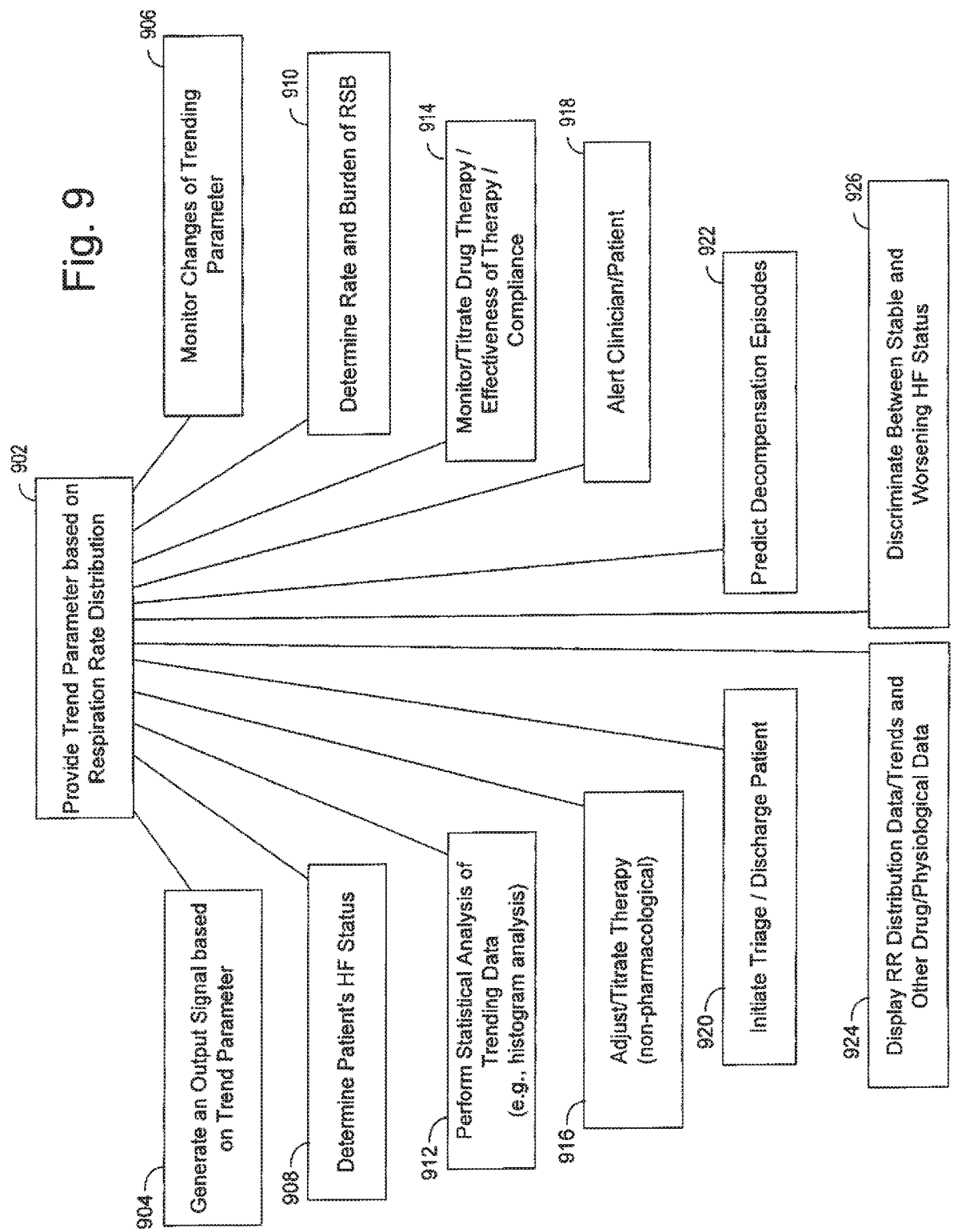
FIG. 9 is a block diagram showing a variety of illustrative operations that may be performed based on a trend parameter generated from a patient's respiration rate distribution in accordance with the present invention.

FIG. 9 is a block diagram showing a variety of illustrative operations that may be performed based on a trend parameter or index 902 generated in accordance with the present invention. As is shown in FIG. 9, the trend parameter may be used to generate 904 a signal indicative of the patient's HF status. The signal may take several forms, including an electrical or electromagnetic signal, optical signal, or acoustic signal, for example. This signal may be used for a variety of diagnostic and therapeutic purposes, including titration of a patient's drug regimen. The signal may be produced by a medical device implanted within the patient. The signal may also be produced by a patient-external device that receives sensor data from a medical device implanted within, or external to, the patient. Other output scenarios are contemplated.

HF status and change in HF status may be determined 908 and monitored 906. Respiration rate and burden resulting from a patient's rapid shallow breathing (e.g., dyspnea) may be determined 910. Rapid shallow breathing (RSB) burden may be computed as the percentage of time a patient experiences RSB per day, average duration of RSB, or other formulation indicating RSB burden on the patient.

Various statistical analyses may be performed 912 on the respiration rate and/or RR distribution data, such as the histogram analyses described hereinabove. Drug therapy may be monitored and titrated 914 based on a trend parameter generated from a patient's respiration rate distribution. Effectiveness of the drug therapy may be quantified using the trend parameter. Patient compliance to a specified drug regimen may also be monitored. The patient and/or clinician may be prompted, such as by audible, textual, or visual means, as to the need for drug administration as originally prescribed or adjusted by the physician. Other types of therapies, such as cardiac or external respiratory therapies (e.g., via a continuous positive airway pressure device), may be adjusted and titrated 916. Patient compliance to a specified therapy may also be monitored.

An alert to the clinician and/or patient may be generated 918 and communicated in various forms to the clinician and/or patient in response to the trend parameter. The trend parameter may be used to initiate triage or discharge 920 a patient from the hospital. The trend parameter may be used to predict decompensation episodes 922. The trend parameter may be used to discriminate 926 between stable and worsening HF status of a patient.

A variety of RR distribution data, trend data, and other drug and physiological data may be displayed 924 for use by the patient, clinician, and/or physician. FIG. 9 is intended to provide a non-exhaustive, non-limiting listing of examples concerning the use of a trend parameter developed using respiration rate distribution data in accordance with the principles of the present invention.

Figure 10:
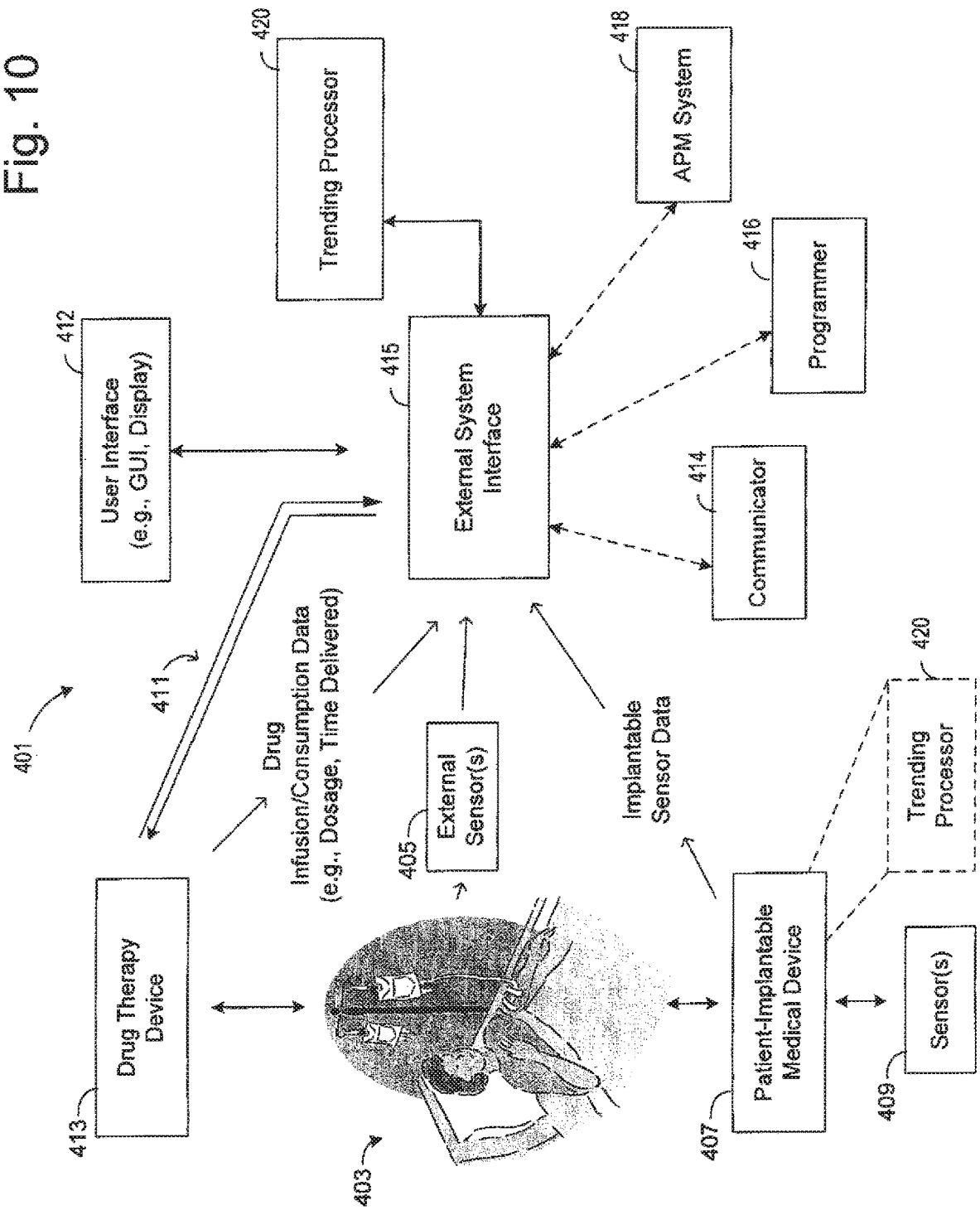
FIG. 10 is a block diagram of a system for managing patient drug delivery based on a trend parameter generated from a patient's respiration rate distribution in accordance with the present invention.

FIG. 10 is a block diagram of a system 401 for managing patient drug delivery based on a trend parameter developed using respiration rate distribution data in accordance with the principles of the present invention. FIG. 10 shows a patient 403 that is receiving drug therapy as prescribed by a physician. The drug therapy may be delivered to the patient 403 by infusion using a drug therapy device 413, such as a drug pump device. The drug therapy may also be delivered by patient consumption of the prescribed medication, in which case the drug therapy device 413 may represent a pill counting device or drug consumption questionnaire, for example.

The system 401 shown in FIG. 10 includes a patient-implantable medical device 407 that is implanted in the patient 403, it being understood that PIMD 407 may alternatively be a patient-external medical device. PIMD 407 incorporates or is coupled to one or more implantable sensors 409. One or more of the sensors 409 are configured to sense a respiratory parameter of the patient's breathing. Such sensors 409 may include one or more of a minute ventilation sensor, transthoracic impedance sensor, accelerometer, or other sensor capable of producing a respiratory waveform representative of the patient's breathing. A variety of external sensors 405 may also be used to sense various physiological parameters of the patient. Such external sensors 405 may include one or more of a pulse oximetry sensor, blood pressure sensor, patient temperature sensor, EKG sensor arrangement, among others.

The system 401 includes a number of patient-external devices. An external system interface 415 includes communication circuitry configured to effect communications with PIMD 407. External system interface 415 may also be configured to effect communications with the drug therapy device 413, such as by a unidirectional or bi-directional communication link. External system interface 415 may further be configured to effect communications with external sensors 405.

Uni-directional communications facilitates the transfer of drug therapy information (e.g., drug type, dosage, day/time of administration) from the drug therapy device 413 to the external system interface 415. It is understood that the external system interface 415 may be integral to, or separate from, the drug therapy device 413 in various embodiments. Bi-directional communications facilitates closed-loop management of the patient's drug therapy, which preferably allows for physician input/intervention within the loop established between the drug therapy device 413 and PIMD 407. This system configuration advantageously allows for automatic or semi-automatic titration of a drug therapy delivered to a patient.

The external system interface 415 may be communicatively coupled to, or integral with, one or more of a programmer 416, an advanced patient management system 418, a portable or hand-held communicator 414, or other patient-external system. The external system interface 415 is coupled to a user interface 412, such as a graphical user interface or other interface that provides a display. User interface 412 preferably includes a user actuatable input/output device, such as a keyboard, touch screen sensor, mouse, light pen, and the like. The user interface 412 may be used to input drug therapy information, such as type of drug(s) being administered, dosage of such drugs, times and dates of drug administration, patient information, including patient weight, perception of wellness, and other information relevant to the patient's condition or drug regimen.

A trending processor 420 is shown coupled to the external system interface 415. Alternatively, trending processor 420 may be incorporated as a component of the PIMD 407, as is shown in phantom. The trending processor 420 may also be incorporated as a component of the communicator 414, programmer 416, or an advanced patient management (APM) system 418. The trending processor 420 performs the various processes described above and provides one or more trend parameters developed from RR distribution data to the external system interface 415 for display to the physician, clinician, and/or patient via the user interface 412, for example.

Various embodiments described herein may be used in connection with devices that provide for HF monitoring, diagnosis, and/or therapy. A patient implantable medical device or PIMD of the present invention may incorporate HF features involving dual-chamber or bi-ventricular pacing/therapy, cardiac resynchronization therapy, cardiac function optimization, or other HF related methodologies. For example, a PIMD of the present invention may incorporate features of one or more of the following references: U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of the present invention, are disclosed in commonly owned U.S. Pat. Nos. 5,313,953; 5,388,578; and 5,411,031, which are hereby incorporated herein by reference.

Figure 11:
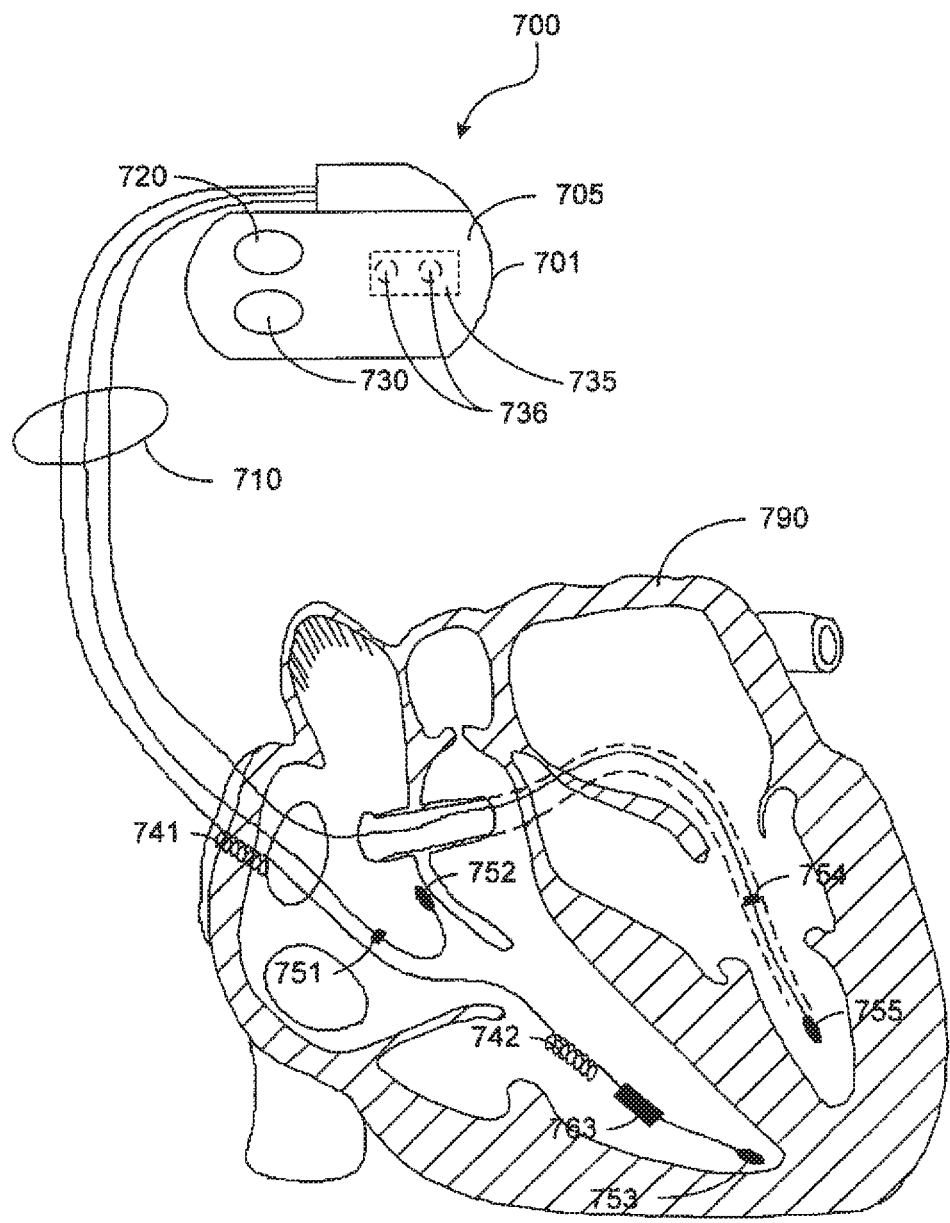
FIG. 11 is an illustration of an implantable cardiac device including a lead assembly shown implanted in a sectional view of a heart, the implantable cardiac device implemented to sense one or more respiratory parameters of a patient in accordance with embodiments of the invention.

Referring now to FIG. 11, there is illustrated an embodiment of a PIMD configured to sense one or more respiratory parameters for purposes of detecting a patient's respiration rate from which a trend parameter may be developed from RR distribution data in accordance with embodiments of the present invention. In this illustrative example, the PIMD includes a cardiac rhythm management device (CRM) 700 including an implantable pulse generator 705 electrically and physically coupled to an intracardiac lead system 710.

Portions of the intracardiac lead system 710 are inserted into the patient's heart 790. The intracardiac lead system 710 includes one or more electrodes and/or sensors configured to sense electrical cardiac activity of the heart, deliver electrical stimulation to the heart, sense the patient's transthoracic impedance, sense transthoracic total impedance, sense blood (internal filling) pressure, flow, and/or temperature, sense acceleration and/or body acoustics, and/or sense other physiological parameters of interest. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to develop respiration waveforms from which various respiratory parameters may be developed.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 11, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 11 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, which are hereby incorporated herein by reference.

For purposes of illustration, and not of limitation, various embodiments of devices implemented in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned US Patent Publication 2004/0230230, and U.S. Pat. No. 7,499, 750, which are hereby incorporated herein by reference.

Figure 12:
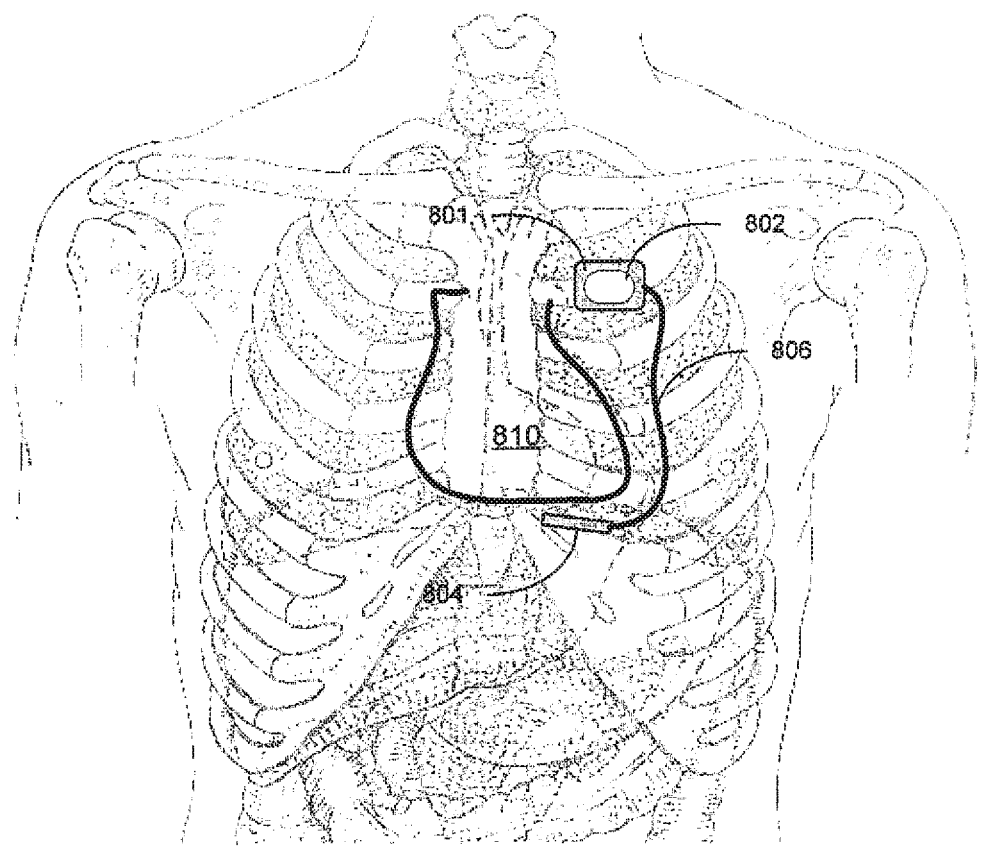
FIG. 12 is an illustration of an implantable medical device including a subcutaneous, non-intrathoracic lead assembly shown implanted outside the ribcage, the implantable medical device implemented to sense one or more respiratory parameters of a patient in accordance with embodiments of the invention.

In one configuration, as is illustrated in FIG. 12, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation. For example, portions of the housing 801 may be covered with a non-conductive, or otherwise electrically resistive, material to direct current flow. Suitable non-conductive material coatings include those formed from silicone rubber, polyurethane, or parylene, for example.

The PIMD system shown in FIG. 12 incorporates one or more sensors configured to sense a parameter useful for detecting respiration. A sensor may be disposed on housing 801, such that element 802 may be representative of such sensor(s) alone or in combination with a can electrode. A sensor(s) may be disposed on another component of the PIMD system, such as on lead 806, a lead separate from lead 806, or on the subsystem element 804, which may be representative of such sensor(s) alone or in combination with a cardiac electrode.

A PIMD of the present invention may be implemented to communicate with a patient management server or network via an appropriate communications interface or an external programmer. A PIMD of the present invention may be used within the structure of an APM system. The advanced patient management system allows physicians to remotely and automatically monitor cardiac and respiratory functions, as well as other patient conditions.

In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a PIMD or a patient-external medical device. It is understood that a wide variety of PIMDs and other implantable and patient-external respiratory and/or cardiac monitoring and/or stimulation device configurations are contemplated, ranging from relatively sophisticated to relatively simple designs. As such, a particular PIMD or patient-external medical device of the present invention may include particular features as described herein, while other such device configurations may exclude particular features described herein.

Various modifications and additions can be made to the preferred embodiments discussed hereinabove without departing from the scope of the present invention. For example, the methods and systems described herein generally include an implantable device or sensor for sensing respiratory parameters and/or computing a patient's respiration rate and/or respiration rate distribution. It is understood that methods and systems of the present invention may be implemented using patient-external devices and sensors, and that the embodiments described herein may be implemented in the context of such patient-external devices and sensors. Accordingly, the scope of the present invention should not be limited by the particular embodiments described above, but should be defined only by the claims set forth below and equivalents thereof.

What is claimed is:
1. A medical status assessment method, comprising:
detecting patient respiration using one or more sensors connected to a medical device;
determining a measure of patient respiration and a plurality of respiration rates based on the detected patient respiration;
determining a distribution of the plurality of respiration rates, wherein the distribution indicates a frequency of occurrence of different respiration rates;
generating a trend parameter based on a measure of spread of the respiration rate distribution and the measure of patient respiration using a processing unit;
discriminating between a stable heart failure status and a decompensated heart failure status of the patient using the trend parameter;
storing the trend parameter in a memory of the processing unit, and automatically titrating patient therapy based on the trend parameter using the processing unit; and outputting a signal indicative of the heart failure status of the patient based on the trend parameter.

2. The method of claim 1, further comprising:
predicting patient decompensation episodes; and
outputting a signal that is related to the predicted decompensation episodes.

3. The method of claim 1,
wherein determining the measure of patient respiration includes determining a characteristic respiration rate, and generating the trend parameter includes based on the measure of spread of the respiration rate distribution and the characteristic respiration rate.

4. The method of claim 1, wherein determining the measure of spread of the distribution of the plurality of respiration rates includes using a standard deviation calculation.

5. The method of claim 1, wherein the trend parameter includes a rapid shallow breathing (RSB) trend parameter, the method further comprising:
predicting patient decompensation episodes using the RSB trend parameter; and
outputting a signal that is related to the predicted decompensation episodes.

6. The method of claim 1, further comprising providing an alert when the heart failure status of the patient is indicative of a worsening of the heart failure status.

7. A method, comprising:
detecting respiration of a patient over a period of time of one day or more using one or more sensors connected to a medical device;
computing a plurality of respiration rates over the period of time based on the detected patient respiration;
determining a measure of patient respiration and a distribution of the respiration rates based on the plurality of respiration rates, wherein a measure of spread of the distribution is calculated using a standard deviation calculation;
generating a Rapid Shallow Breathing (RSB) trend parameter based on the measure of spread of the respiration rate distribution and the measure of patient respiration, and automatically titrating patient therapy based on the RSB trend parameter using the processing unit; and
discriminating between a stable heart failure status and a decompensated heart failure status of the patient using the RSB trend parameter.

8. The method of claim 7, further comprising:
determining a rapid shallow breathing (RSB) burden for the patient based on an average duration of RSB; and
outputting a signal indicative of a heart failure status of the patient based on the RSB burden.

9. The method of claim 8, wherein determining the RSB burden comprises computing a percentage of time that the patient experiences rapid shallow breathing.

10. The method of claim 7, further comprising:
predicting patient decompensation episodes using the RSB trend parameter with the processing unit; and
outputting a signal from an output port of the processing unit that is related to the predicted decompensation episodes.

11. The method of claim 7, further comprising generating an alert based on the discriminated stable or decompensated heart failure status.

12. The method of claim 7, wherein detecting respiration of the patient is performed using one or more sensors of an implantable device.

13. The method of claim 7, wherein the patient therapy includes one or more of cardiac therapy, respiratory therapy or drug therapy.

14. A medical status assessment system, comprising:
a medical device coupled to sensing circuitry;
detection circuitry coupled to the sensing circuitry, the detection circuitry configured to detect at least one respiratory parameter of a patient;
a memory;
a processor coupled to the detection circuitry, the processor configured to:
compute a measure of patient respiration and a plurality of respiration rates based on the detected patient respiratory parameter,
determine a distribution of the respiration rates, wherein the distribution indicates a frequency of occurrence of different respiration rates,
generate a trend parameter based on a measure of spread of the respiration rate distribution and the measure of patient respiration, and adjust patient therapy based on the trend parameter; and
discriminate between a stable heart failure status and a decompensated heart failure status of the patient using the trend parameter,
wherein, to generate the trend parameter, the processor is configured to generate a rapid shallow breathing (RSB) trend parameter of the patient based on the respiration rate distribution, and to adjust patient therapy, the processor is configured to automatically titrate patient therapy based on the RSB trend parameter.

15. The system of claim 14, wherein the measure of patient respiration includes a characteristic respiration rate.

16. The system of claim 14, wherein the medical device comprises a patient implantable medical device.

17. The system of claim 14, wherein the processor is further configured to:
characterize a heart failure status of the patient based on the trend parameter; and
determine a rapid shallow breathing (RSB) burden of the patient based on an average duration of RSB.

* * * * *